(12) United States Patent
Lee et al.

(10) Patent No.: US 7,070,989 B2
(45) Date of Patent: Jul. 4, 2006

(54) ESCHERICHIA COLI STRAIN SECRETING HUMAN GRANULOCYTE COLONY STIMULATING FACTOR (G-CSF)

(75) Inventors: Sang-Yup Lee, Taejon (KR); Ki-Jun Jeong, Taejon (KR)

(73) Assignee: Korea Advanced Institute of Science and Technology (KR)

( * ) Notice: Subject to any disclaimer, the term of this patent is extended or adjusted under 35 U.S.C. 154(b) by 552 days.

(21) Appl. No.: 10/009,792

(22) PCT Filed: Mar. 31, 2001

(86) PCT No.: PCT/KR01/00549

§ 371 (c)(1),
(2), (4) Date: Dec. 13, 2001

(87) PCT Pub. No.: WO01/73081

PCT Pub. Date: Oct. 4, 2001

(65) Prior Publication Data

US 2003/0153049 A1   Aug. 14, 2003

(30) Foreign Application Priority Data

Mar. 31, 2000   (KR) .................. 10-2000-0017052

(51) Int. Cl.
*C12N 15/00*  (2006.01)
*C12N 15/09*  (2006.01)
*C12N 15/64*  (2006.01)
*C12N 15/74*  (2006.01)
*C12P 21/06*  (2006.01)

(52) U.S. Cl. ................ 435/320.1; 435/71.1; 435/69.6; 435/69.3; 435/69.1; 435/91.4; 435/471; 435/476

(58) Field of Classification Search ............ 435/320.1, 435/71.1, 71.2, 69.6, 69.3, 69.1, 91.4, 471, 435/476
See application file for complete search history.

(56) References Cited

OTHER PUBLICATIONS

Bong Hyun Chung, et al "Overproduction of Human Granulocyte-Colony Stimulating Factor Fused to the PelB Signal Peptide in *Escherichia coli*." J Ferment Bioeng., 85(4) 443-446 (1998).
Julian Pérez-Pérez, et al. "DnaK/DnaJ Supplementation Improves the Periplasmic Production of Human Granulocyte-Colony Stimulating Factor in *Escherichia coli*." Biochem. Biophys. Res. Commun., 210(2):524-529 (1995).

*Primary Examiner*—S. Devi
(74) *Attorney, Agent, or Firm*—Knobbe, Martens, Olson & Bear, LLP

(57) ABSTRACT

The present invention provides a recombinant plasmid vector comprising a kanamycin resistance gene, a promoter, an endoxylanase signal sequence, a nucleotide sequence coding for an oligopeptide consisting of 13 amino acids including 6 consecutive histidine residues, and a human granulocyte colony stimulating factor(hG-CSF) gene; an *E. coli* transformed with the said vector; and, a process for producing complete hG-CSF protein with high purity from the protein pool secreted by the said microorganism. In accordance with the invention, the hG-CSF protein can be prepared with high purity through rather simple process facilitating secretion of large amount of hG-CSF fusion protein into the periplasm, which does not require complicated processes such as solubilization and subsequent refolding required for isolation of the hG-CSF protein produced in cytoplasm as insoluble inclusion bodies by conventional techniques, thus, the hG-CSF protein can be widely used as an active ingredient in the development of supplementary agents for anticancer therapy.

13 Claims, 13 Drawing Sheets

```
  1 ATG GCT GGA CCT GCC ACC CAG AGC CCC ATG AAG CTG ATG GCC CTG   45
 46 CAG CTG CTG GGC CTG TGG AGT GCA CTC TGG ACA GTG CAG GAA GCC   90
 91 CCC CTG CCT GCC AGC AGC CAG AGC ACA CAG TTC CAG GCA GCG CTC  135
136 TGC TTA GAG AAG CTG CAA ATC AAG GAT GGC TTC GGC CTC TCG GCG  180
181 CAG CTC CTC TAC CAG CTG TGC TTG CAG GGG CTC GAA CAT AGC TCC  225
226 TTC CTC TTG GGT ACC TTG GAC CAG ACA CTG GAC TTG GGA GAC GTC  270
271 GAG TTG GCC ACC ATC CCC CAG CAG GCC ATG GAA CTG GGA TTC GCC  315
316 TTT GCC CCT CTG CAG CCC CAG GGT ATG GCC CCG TCC TTT GCC TCT  360
361 CCT GCC TTC CAG CGC CGG CTG GAG ATG CTA GTT GCC CTG CAT CTG  405
406 GCT TTC CAG CGC CAG GCA GGA GAC CGC TAC TCG CTA CGC CTT GCC  450
451 CAG AGC TTC CTG CTG CGC GAG GTG TCG CGT CTT GTT CTA CAC CTT  495
496 CAG CCC TAA TAA                                              508
                  ─── ───
                  stop codon     (see: SEQ ID NO: 17)
```

FIG. 1

```
      -30                                                      -16
  1 ATG GCT GGA CCT GCC ACC CAG AGC CCC ATG AAG CTG ATG GCC CTG  45

-15                                                -1  +1
 46 CAG CTG CTG CTG TGG AGT GCA CTC TGG ACA GTG CAG GAA GCC ACC  90
                                                            Thr 2                                                       16
 91 CCC CTG GGC CCT GCC AGC TCC CTG CCC CAG AGC TTC CTG CTC AAG 135
    Pro Leu Gly Pro Ala Ser Ser Leu Pro Gln Ser Phe Leu Leu Lys 17                                                       31
136 TGC TTA GAG CAA GTG AGG AAG ATC CAG GGC GAT GGC GCA GCG CTC 180
    Cys Leu Glu Gln Val Arg Lys Ile Gln Gly Asp Gly Ala Ala Leu 32                                                       46
181 CAG GAG AAG CTG TGT GCC ACC TAC AAG CTG TGC CAC CCC GAG GAG 225
    Gln Glu Lys Leu Cys Ala Thr Tyr Lys Leu Cys His Pro Glu Glu 47                                                       61
226 CTG GTG CTG CTC GGA CAC TCT CTG GGC ATC CCC TGG GCT CCC CTG 270
    Leu Val Leu Leu Gly His Ser Leu Gly Ile Pro Trp Ala Pro Leu 62                                                       76
271 AGC AGC TGC CCC AGC CAG GCC CTG CAG CTG GCA GGC TGC TTG AGC 315
    Ser Ser Cys Pro Ser Gln Ala Leu Gln Leu Ala Gly Cys Leu Ser 77                                                       91
316 CAA CTC CAT AGC GGC CTT TTC CTC TAC CAG GGG CTC CTG CAG GCC 360
    Gln Leu His Ser Gly Leu Phe Leu Tyr Gln Gly Leu Leu Gln Ala 92                                                      106
361 CTG GAA GGG ATC TCC CCC GAG TTG GGT CCC ACC TTG GAC ACA CTG 405
    Leu Glu Gly Ile Ser Pro Glu Leu Gly Pro Thr Leu Asp Thr Leu 107                                                      121
406 CAG CTG GAC GTC GCC GAC TTT GCC ACC ACC ATC TGG CAG CAG ATG 450
    Gln Leu Asp Val Ala Asp Phe Ala Thr Thr Ile Trp Gln Gln Met 122                                                      136
451 GAA GAA CTG GGA ATG GCC CCT GCC CTG CAG CCC ACC CAG GGT GCC 495
    Glu Glu Leu Gly Met Ala Pro Ala Leu Gln Pro Thr Gln Gly Ala 137                                                      151
496 ATG CCG GCC TTC GCC TCT GCT TTC CAG CGC CGG GCA GGA GGG GTC 540
    Met Pro Ala Phe Ala Ser Ala Phe Gln Arg Arg Ala Gly Gly Val 152                                                      166
541 CTA GTT GCC TCC CAT CTG CAG AGC TTC CTG GAG GTG TCG TAC CGC 585
    Leu Val Ala Ser His Leu Gln Ser Phe Leu Glu Val Ser Tyr Arg 167                         174
586 GTT CTA CGC CAC CTT GCC CAG CCC TAA TAA                     616
    Val Leu Arg His Leu Ala Gln Pro stop codon (see: SEQ ID NO: 18)
    (see: SEQ ID NO: 19)                            FIG. 3
```

```
     1                                                                      15
  1 ATG ACC CCC CTG GGC CCT GCC AGC TCC CTG CCC CAG AGC TTC CTG  45
    Met Thr Pro Leu Gly Pro Ala Ser Ser Leu Pro Gln Ser Phe Leu 16                                                                     30
 46 CTC AAG TGC TTA GAG CAA GTG AGG AAG ATC CAG GGC GAT GGC GCA  90
    Leu Lys Cys Leu Glu Gln Val Arg Lys Ile Gln Gly Asp Gly Ala 31                                                                     45
 91 GCG CTC CAG GAG AAG CTG TGT GCC ACC TAC AAG CTG TGC CAC CCC 135
    Ala Leu Gln Glu Lys Leu Cys Ala Thr Tyr Lys Leu Cys His Pro 46                                                                     60
136 GAG GAG CTG GTG CTG CTC GGA CAC TCT CTG GGC ATC CCC TGG GCT 180
    Glu Glu Leu Val Leu Leu Gly His Ser Leu Gly Ile Pro Trp Ala 61                                                                     75
181 CCC CTG AGC AGC TGC CCC AGC CAG GCC CTG CAG CTG GCA GGC TGC 225
    Pro Leu Ser Ser Cys Pro Ser Gln Ala Leu Gln Leu Ala Gly Cys 76                                                                     90
226 TTG AGC CAA CTC CAT AGC GGC CTT TTC CTC TAC CAG GGG CTC CTG 270
    Leu Ser Gln Leu His Ser Gly Leu Phe Leu Tyr Gln Gly Leu Leu 91                                                                    105
271 CAG GCC CTG GAA GGG ATC TCC CCC GAG TTG GGT CCC ACC TTG GAC 315
    Gln Ala Leu Glu Gly Ile Ser Pro Glu Leu Gly Pro Thr Leu Asp 106                                                                   120
316 ACA CTG CAG CTG GAC GTC GCC GAC TTT GCC ACC ACC ATC TGG CAG 360
    Thr Leu Gln Leu Asp Val Ala Asp Phe Ala Thr Thr Ile Trp Gln 121                                                                   135
361 CAG ATG GAA GAA CTG GGA ATG GCC CCT GCC CTG CAG CCC ACC CAG 405
    Gln Met Glu Glu Leu Gly Met Ala Pro Ala Leu Gln Pro Thr Gln 136                                                                   150
406 GGT GCC ATG CCG GCC TTC GCC TCT GCT TTC CAG CGC CGG GCA GGA 450
    Gly Ala Met Pro Ala Phe Ala Ser Ala Phe Gln Arg Arg Ala Gly 151                                                                   165
451 GGG GTC CTA GTT GCC TCC CAT CTG CAG AGC TTC CTG GAG GTG TCG 495
    Gly Val Leu Val Ala Ser His Leu Gln Ser Phe Leu Glu Val Ser 166                        175
496 TAC CGC GTT CTA CGC CAC CTT GCC CAG CCC TAA TAA              531
    Tyr Arg Val Leu Arg His Leu Ala Gln Pro stop codon (see: SEQ ID NO: 20)
(see: SEQ ID NO: 21)
```

FIG. 5

```
1                                                              15
1 ATG ACT CCG TTA GGT CCA GCC AGC TCC CTG CCC CAG AGC TTC CTG  45
  Met Thr Pro Leu Gly Pro Ala Ser Ser Leu Pro Gln Ser Phe Leu (see: SEQ ID NO: 22)
(see: SEQ ID NO: 23)
```

FIG. 7

```
    -28                                                     -14
 1  ATG TTT AAG TTT AAA AAG AAA TTC TTA GTG GGA TTA ACG GCA GCT   45
    Met Phe Lys Phe Lys Lys Lys Phe Leu Val Gly Leu Thr Ala Ala

-13                                         -1  +1       2
46  TTC ATG AGT ATC AGC ATG TTT TCT GCA ACC GCC TCT GCA ACT CCG   90
    Phe Met Ser Ile Ser Met Phe Ser Ala Thr Ala Ser Ala Thr Pro 3                                                      17
91  TTA GGT CCA GCC AGC TCC CTG CCC CAG AGC TTC CTG CTC AAG TGC   135
    Leu Gly Pro Ala Ser Ser Leu Pro Gln Ser Phe Leu Leu Lys Cys
```

(see: SEQ ID NO: 24)
(see: SEQ ID NO: 25)

FIG. 9

```
                                    -28                                                            -14
                                  1 ATG TTT AAG TTT AAA AAG AAA TTC TTA GTG GGA TTA ACG GCA GCT    45
                                    Met Phe Lys Phe Lys Lys Lys Phe Leu Val Gly Leu Thr Ala Ala

-13                                         -1  +1   2
                                 46 TTC ATG AGT ATC AGC ATG TTT TCT GCA ACC GCC TCT GCA GCT GGC    90
                                    Phe Met Ser Ile Ser Met Phe Ser Ala Thr Ala Ser Ala Ala Gly 3                                          17
                                 91 CCG CAC CAT CAC CAT ATC GAG GGA AGG ACT CCG TTA GGT           135
                                    Pro His His His His His Ile Glu Gly Arg Thr Pro Leu Gly 18                                          32
                                136 CCA GCC AGC TCC CTG CCC CAG AGC TTC CTG CTC AAG TGC TTA GAG   180
                                    Pro Ala Ser Ser Leu Pro Gln Ser Phe Leu Leu Lys Cys Leu Glu (see: SEQ ID NO: 26)
                                (see: SEQ ID NO: 27)
```

FIG. 12

ESCHERICHIA COLI STRAIN SECRETING HUMAN GRANULOCYTE COLONY STIMULATING FACTOR (G-CSF)

This application is the U.S. National Phase under 35 U.S.C. § 371 of International Application PCT/KR01/00549, filed Mar. 31, 2001, which claims priority of KR 2000/17052, filed Mar. 31, 2000.

BACKGROUND OF THE INVENTION

1. Field of the Invention

The present invention relates to an *E. coli* producing and secreting human granulocyte-colony stimulating factor(hG-CSF), more specifically, to a recombinant plasmid constructed to express secretory hG-CSF in *E. coli*, an *E. coli* transformed with the said plasmid to secrete hG-CSF, and a process for preparing hG-CSF using the said transformed *E. coli*.

2. Description of the Prior Art

Colony stimulating factors(CSFs) known to be synthesized by various cell types such as mononuclear macrophages, T-lymphocytes, and fibroblasts are found in the various parts of normal human body. CSFs are classified into three major categories, granulocyte-colony stimulating factor(G-CSF), macrophage-colony stimulating factor(M-CSF) and granulocyte/macrophage-colony stimulating factor(GM-CSF), among them, G-CSF is an essential protein in manufacturing blood cells via promoting proliferation and differentiation of hemopoietic stem cells, and facilitates increase in numbers of granulocytes, especially, neutrophils which play an important role in the protection of the body from the infection. Chemotherapies widely used to treat growing tumors not only inhibit the growth of tumors but also inhibit the production of neutrophils, giving rise to severe side effects due to the diminished protecting function of neutrophils. Administration of G-CSF to the patients under such chemotherapies is known to be an effective way of treatment and prevention of the infectious diseases by means of facilitating the increase in neurophil numbers.

In 1986, the hG-CSF gene was isolated from a human squamous carcinoma cell line CHU-II, its nucleotide sequence was first determined and expressed in COS cells by Nagata et al. (see: Nagata et al., *Nature* 319: 415 (1986)). The hG-CSF is a glycoprotein comprising 30 signal peptides which consists of 174 amino acid residues. The hG-CSF includes 5 cysteine residues of which 4 cysteines form two disulfide bonds, between Cys-36 and Cys-64, and between Cys-64 and Cys-74, which serve for folding of the expressed protein and its activity (see: Hill et al., *Proc. Natl. Acad. Sci., USA*, 90:5167–5171(1993)). The hG-CSF dose not have the consensus sequence(Asn-X-Thr/Ser) for N-glycosylation, but O-glycosylation occurs at Thr-133. However, the recombinant G-CSF produced in *E. coli* is known to have almost the same biological activities as natural G-CSF, which means glycosylation is unnecessary for the G-CSF activity.

With the recent progress in recombinant DNA technology, G-CSF can be produced in bacteria, plant cells and animal cells, and some results previously reported are described here: Souza et al. isolated a cDNA from the human bladder cancer cell line 5637, determined its sequence and reported its expression in *E. coli* (see: Souza et al., *Science*, 232:61 (1986)). Moreover, researches on production of hG-CSF in *E. coli*, plant cells and animal cells, and on construction and production of hG-CSF derivatives have been reported. However, technologies known to date for the production of hG-CSF in *E. coli* have many disadvantages in terms of protein yield or production cost since the hG-CSF is produced in cytoplasm in the form of insoluble inclusion body, which requires subsequent solubilization and renaturation to obtain biologically active form of hG-CSF protein. Although small quantity of soluble hG-CSF can be isolated directly, such method still have limitations in a sense that the active fraction of hG-CSF protein has to be isolated from the pool of enormous amounts of *E. coli* proteins.

In general, proteins secreted to the periplasm of *E. coli* carry signal sequence, which is found in all proteins transportable out of the cytoplasm, and cleaved off by signal peptidase in the periplasm. The signal sequence is essential in secreting proteins in *E. coli*. Therefore, recombinant proteins originally not encoded by *E. coli* genes can be secreted into the periplasm or to the extracellular broth by joining known signal sequence(OmpA, OmpF, PelB, PhoA, SpA, etc.), as it is or with slight modifications, to the N-terminus of gene coding an exogenous protein.

The method for production of hG-CSF by secretion into the periplasmic space has following advantages over the conventional method by producing in cytoplasm described above: first, it is easy to isolate and purify the recombinant proteins, with high purity, in periplasm than in cytoplasm, since there are fewer proteins in periplasm than in cytoplasm (see: Nossal, N. G. et al., *J. Biol. Chem.*, 241:3055–3062 (1966)); secondly, recombinant proteins secreted into periplasm are segregated from the cytoplasm where the most proteases are found, obtaining high yield in production of recombinant protein by avoiding degradation of the protein by proteases present in cytoplasm (see: Meerman and Georgiou, *Ann. N.Y. Acad. Sci.*, 721:292–302(1994)); thirdly, the bacterial periplasm is more oxidizing environment than cytoplasm, conducting disulfide bond formation and correct folding of polypeptide easily, thus, the formation of insoluble aggregates is avoidable (see: Hockney, *TIBTECH*, 12:456–463(1994)).

Having such advantages, the method resulting in secretion of recombinant proteins into the periplasm has been employed for production of hG-CSF in *E. coli* and reported as follows: Perez-Perez et al. have tried to get secreted form of hG-CSF, employing OmpA which is one of the signal sequences in *E. coli*, without success. To solve that problem, they employed the system for coexpression of two molecular chaperones, DnaK and DnaJ, and merely obtain a small quantity of secreted hG-CSF (see: Perez-Perez et al., *Biochem. Biophys. Res. Commun.*, 210:524–529(1995)); and, Chung et al. have tried to obtain secreted form of hG-CSF employing another signal sequence, PelB, again without success, but hG-CSF was accumulated in the form of insoluble inclusion body in cytoplasm (see: Chung et al., *J. Fermen. Bioengin.*, 85:443–446(1998)).

In view of above situation, there is a continuing need to develop the technique for facilitating secretion of hG-CSF at a substantial level into the periplasm through rather simple process which does not require solubilization of insoluble inclusion body and subsequent refolding.

SUMMARY OF THE INVENTION

The present inventors have made an effort to develop the technique for facilitating secretion of hG-CSF into the periplasm, thus, they have found that *E. coli*, transformed with the recombinant plasmid containing nucleotide sequence coding for oligopeptide consisting of 13 amino acids, *Bascillus*-derived endoxylanase signal sequence and 6 histidine residues, can secrete oligopeptide/hG-CSF fusion protein efficiently so that hG-CSF protein can be produced using the said transformed *E. coli*.

The first object of the present invention is, therefore, to provide the recombinant plasmid constructed for *E. coli* to express and secrete hG-CSF fusion protein therefrom.

The second object of the invention is to provide transformed *E. coli* with the said plasmid.

The third of the invention is to provide a process for producing hG-CSF protein employing the said microorganism.

BRIEF DESCRIPTION OF THE DRAWINGS

The above, the other objects and features of the invention will become apparent from the following descriptions given in conjunction with the accompanying drawings, in which:

FIG. 1 is the nucleotide sequence of hG-CSF gene inserted into the plasmid p19CSF.

FIG. 3 is the nucleotide sequence and the deduced amino acid sequence of hG-CSF gene inserted into the plasmid p19CSFm.

FIG. 5 is the nucleotide sequence and the deduced amino acid sequence of hG-CSF gene inserted into the plasmid pEDCSFm.

FIG. 7 is the nucleotide sequence and the deduced amino acid sequence of the N-terminal portion of hG-CSF gene inserted into the plasmid pEDCSFmII.

FIG. 9 is the nucleotide sequence and the deduced amino acid sequence of the N-terminal portion of hG-CSF gene inserted into the plasmid pTrcSCSFmII.

FIG. 12 is the nucleotide sequence and the deduced amino acid sequence of the N-terminal portion of hG-CSF gene inserted into the plasmid pTHSCSFmII.

DETAILED DESCRIPTION OF THE INVENTION

Figure 2:
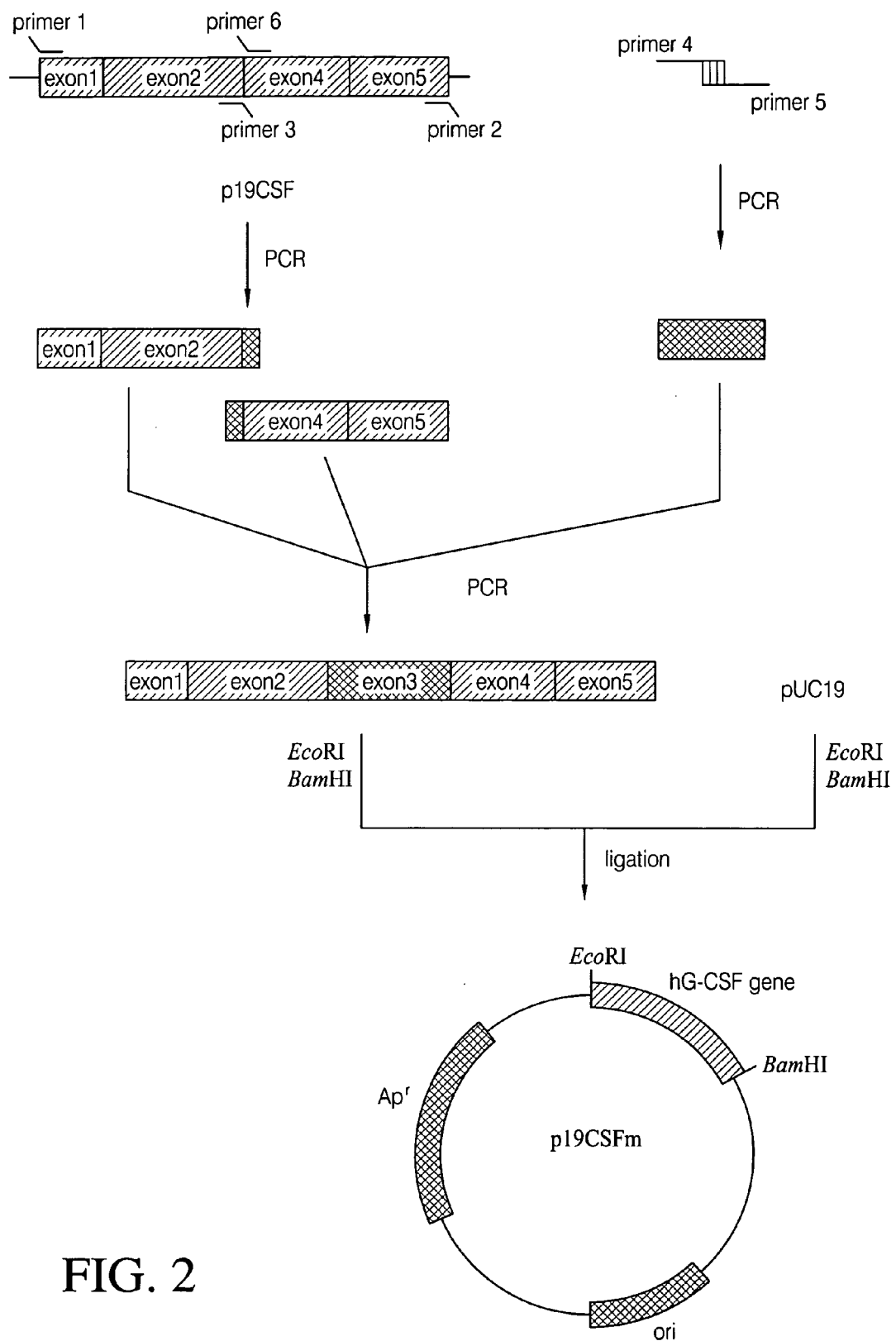
FIG. 2 shows a construction scheme and a genetic map for the plasmid p19CSFm.

The recombinant plasmid of the invention designed for secreting hG-CSF fusion protein efficiently from *E. coli* contains: a kanamycin resistance gene, an endoxylanase signal sequence, a nucleotide sequence coding for an oligopeptide consisting of 13 amino acid residues including 6 consecutive histidine residues, a modified hG-CSF gene and Trc promoter. The recombinant *E. coli* of the invention secreting hG-CSF protein efficiently is prepared by transformation of *E. coli* with the said recombinant plasmid. The hG-CSF protein can be prepared with high purity by isolating the hG-CSF fusion protein from the protein pool obtained from the transformed *E. coli* using a Ni-column and subsequent protease treatment.

The present invention is illustrated in more detail as followings.

First, the recombinant plasmid vector pTHKCSFmII, containing cDNA encoding hG-CSF protein, endoxylanase signal sequence for hG-CSF protein secretion, Trc promoter which is a strong inducible promoter, kanamycin resistance gene encoding non-secretory protein, and a nucleotide sequence encoding an oligopeptide consisting of 13 amino acid residues including 6 consecutive histidine residues between endoxylanase signal sequence and hG-CSF polypeptide, is constructed for preparing transformed *E. coli* which expresses and secretes hG-CSF fusion protein into the periplasm: wherein, cDNA encoding hG-CSF protein is obtained by joining 3rd exon-deleted hG-CSF cDNA obtained from a human breast carcinoma cDNA library to the synthesized 3rd exon, *Bacillus* sp.-derived endoxylanase signal sequence is employed for facilitating secretion of hG-CSF protein from *E. coli*, and kanamycin resistance gene is employed as a selection marker. Furthermore, to prevent cell lysis occurred during the secretion of hG-CSF protein in *E. coli*, a nucleotide sequence encoding an oligopeptide consisting of 13 amino acid residues including 6 consecutive histidine residues was included between DNA of endoxylanase signal sequence and hG-CSF gene, and the amino acid sequence of the oligopeptide is N'-Ala-Gly-Pro-His-His-His-His-His-His-Ile-Glu-Gly-Arg-C' (SEQ ID NO: 1).

Subsequently, recombinant *E. coli* secreting hG-CSF fusion protein is prepared by introducing the plasmid pTHKCSFmII constructed above into *E. coli*: wherein, *E. coli* strains BL21(DE3), HB101, MC4100, W3110 and XL1-Blue, preferably MC4100, can be used. *E. coli* MC4100 transformed with the recombinant plasmid pTHKCSFmII was named *E. coli* MC4100/pTHKCSFmII (*Escherichia Coli* MC4100/pTHKCSFmII), which was deposited with the Korean Collection for Type Cultures(KCTC) affiliated to Korea Research Institute of Bioscience and Biotechnology (KRIBB), an international depository authority, under accession(deposition) No. KCTC 0754BP on Mar. 13, 2000.

Finally, the complete hG-CSF protein is prepared from the protein pool obtained from the transformed *E. coli* using a Ni-column and a protease: the said *E. coli* secretes hG-CSF fusion protein of which N-terminus is linked by an oligopeptide consisting of 13 amino acid residues including 6 consecutive histidine residues. The secreted hG-CSF fusion protein is isolated using a Ni-column to which 6 consecutive histidine residues present in the oligopeptide of the fusion protein can bind, and then the complete hG-CSF protein can be prepared from the hG-CSF fusion protein isolated above by treating a protease to get rid of the oligopeptide. Since the hG-CSF protein has to be non-susceptible to the protease employed, the C-terminal sequence of the oligopeptide should be selected to be cleaved off by the protease of which recognition sequences are not present in the hG-CSF protein. As an example, in the present invention, the C-terminal amino acid sequence of the oligopeptide was selected to be Ile-Glu-Gly-Arg (SEQ ID NO: 28, which is residue numbers 10–13 of SEQ ID NO: 10, which is recognized and cleaved by Factor Xa, a protease not having recognition sequences in hG-CSF protein.

The present invention is further illustrated in the following examples, which should not be taken to limit the scope of the invention.

EXAMPLE 1

Preparation of cDNA for Human Granulocyte-Colony Stimulating Factor(hG-CSF)

To isolate hG-CSF gene, hG-CSF cDNA was prepared by PCR amplification of a human breast carcinoma cDNA library. Nucleotide sequence of the hG-CSF gene was retrieved in the GenBank, and then, primer 1: 5'-GCGAATTCATGGCTGGACCTGCCACCCAG-3' (SEQ ID NO: 2) and primer 2: 5'-GCGGATCCTTATTAGGGCTGGGCAAGGTGGCG-3' (SEQ ID NO: 3) were synthesized, respectively. For the convenience of cloning of PCR product, EcoRI and BamHI restriction sites were introduced at primer 1 and primer 2, respectively. Then, PCR was performed by, employing High Fidelity PCR System (Boehringer Mannheim Co., Germany), under following condition: one cycle of denaturation at 94° C. for 7 min; 30 cycles of denaturation at 94° C. for 1 min, annealing at 50° C. for 1 min, and extension at 72° C. for 1 min; and, one cycle of extension at 72° C. for 7 min. DNA molecules obtained by the PCR were subjected to agarose gel electrophoresis to isolate DNA fragment of approximately 530 bp, which was subsequently digested with EcoRI and BamHI to obtain DNA fragment concerned.

In order to clone the DNA fragment obtained above, the said DNA fragment was joined into the plasmid pUC19 (see: Yanisch-Perron et al., Gene, 33:109–119(1985)) digested with EcoRI and BamHI using T4 DNA ligase, and then, the ligation product was introduced into E. coli XL1-Blue (supE44 hsdR17 recA1 endA1 gyrA96 thi relA1 lacF' (proAB+lacIqlacZΔ M15Tn(tetr))) (see: Bullock, W. O. et al., BioTechniques, 5:376–378(1987)) by electroporation technique to obtain transformed E. coli. The transformants were selected on the LB agar medium containing ampicillin (50 μg/l) and the recombinant plasmid p19CSF was obtained therefrom. The nucleotide sequence of the fragment in p19CSF was determined using automatic DNA sequencer (ABI Prism model 377, Perkin Elmer Co., U.S.A.). It has been found that there was 108 bp deletion in the middle of the cloned fragment of the invention compare to the published nucleotide sequence of hG-CSF gene, meanwhile, the rest sequence of 508 bp was identical to the published sequence of hG-CSF gene (see: FIG. 1). Comparing with the sequence of genomic DNA of hG-CSF, the 108 bp deletion in the fragment of the invention corresponded to the third exon among five exons of hG-CSF gene.

In order to obtain complete sequence of the hG-CSF gene, four primers, primer 3: 5'-TCCTCGGGGTGGCACAGCTTGTAGGTGGCACACAGCTTCTCCTGGAGCGC-3' (SEQ ID NO: 4), primer 4: 5'-GCTGTGCCACCCCGAGGAGCTGGTGCTGCTCGGACACTCTCTGGGCATCC-3' (SEQ ID NO: 5), primer 5: 5'-TGGCTGGGGCAGCTGCTCAGGGGAGCCCAGGGGATGCCCAGAGAGTGTC-3' (SEQ ID NO: 6), and primer 6: 5'-AGCAGCTGCCCCAGCCAGGCCCTGCAGCTGGCAGGCTGCTTGAGCCAA-3' (SEQ ID NO: 7) corresponding the third exon were prepared and PCR was carried out. Using primer 1 and the PCR product obtained above, p19CSF was subjected to PCR amplification, and with the primer 2, PCR was carried out in the same way as with primer 1. Using both PCR products, PCR was performed once again and the resulting product was digested with two restriction enzymes, EcoRI and BamHI, and then the fragments were cloned into the same site of pUC19 as the site used above. The transformed E. coli XL1-Blue were selected on the LB agar medium containing ampicillin (50 μg/l) and the recombinant plasmid p19CSFm was obtained therefrom (see: FIG. 2). The nucleotide sequence of the fragment in p19CSFm was determined and found to be identical to the sequence of the published hG-CSF gene (see: FIG. 3).

EXAMPLE 2

Construction of the Recombinant Plasmid, pEDCSFm

Figure 4:
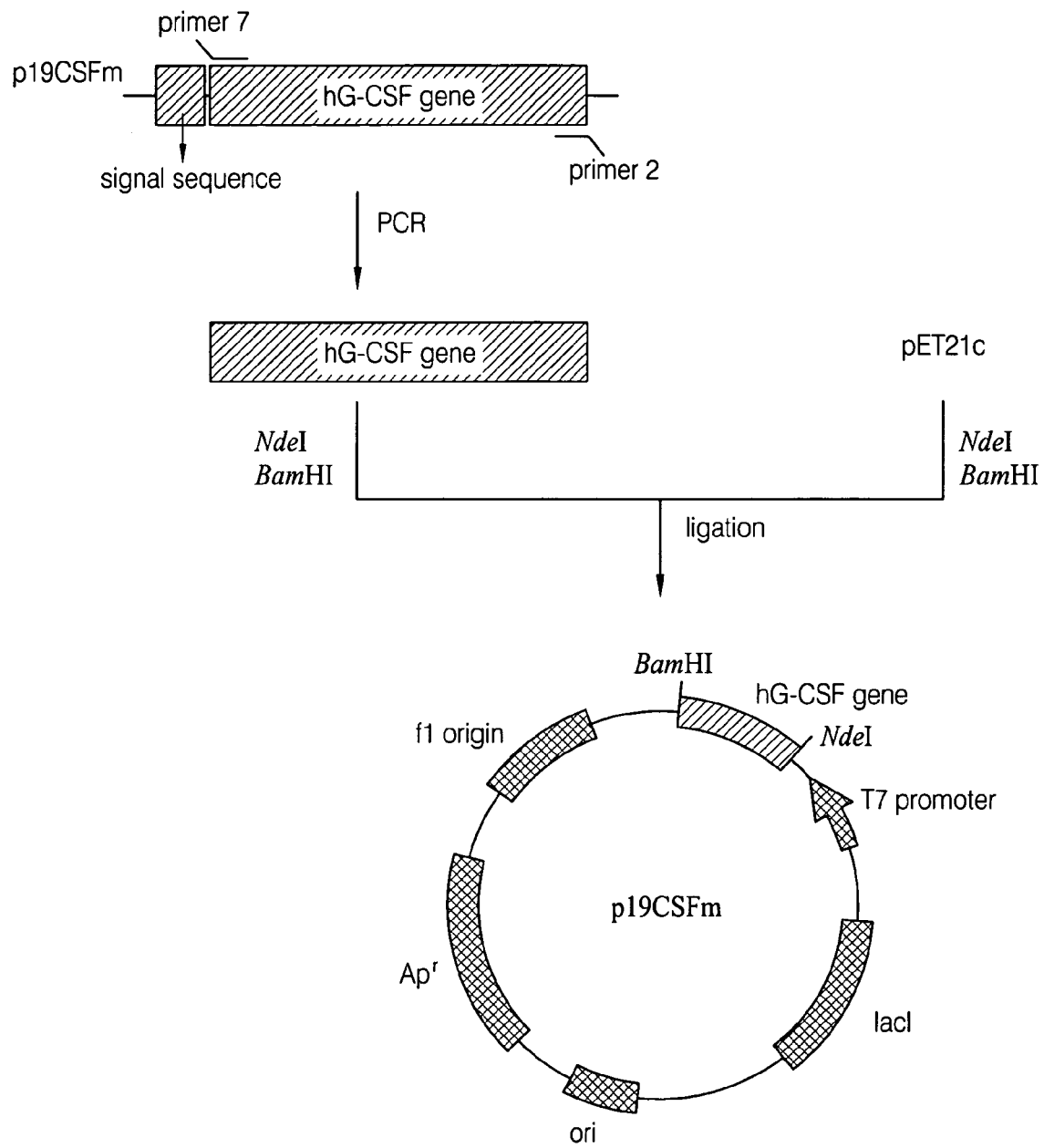
FIG. 4 shows a construction scheme and a genetic map for the plasmid pEDCSFm.

In order to get hG-CSF protein expressed from the hG-CSF gene obtained in Example 1, the mature hG-CSF gene was constructed by removing signal sequence from p19CSFm (see: FIG. 5). To clone the mature hG-CSF gene, Primer 7: 5'-GCGAATTCATATGACCCCCCTGGGCCCTGCCAGC-3' (SEQ ID NO: 8) was prepared. Employing primer 2 and primer 7, p19CSFm was subjected to PCR amplification, and the amplified DNA molecules were digested with two restriction enzymes, NdeI and BamHI. The resultant DNA fragment was joined into the T7 promoter-containing plasmid pET21c (Novagen Co., U.S.A.) digested with NdeI and BamHI. After transformation of E. coli XL1-Blue with the ligated product by electroporation, the transformants were selected on the LB agar medium containing ampicillin (50 μg/l) and the recombinant plasmid, pEDCSFm was obtained therefrom (see: FIG. 4).

For production of hG-CSF protein in E. coli, the recombinant plasmid pEDCSFm was introduced into E. coli BL21 (DE3) (F-ompT hsdSB(rB- mB-) gal dcm (DE3) a prophage carrying the T7 RNA polymerase gene). The transformed E. coli harboring the recombinant plasmid was inoculated into 50 ml of liquid LB medium in a 250 ml flask and incubated at 37° C. When the cell concentration reached to OD600 of about 0.7, 1 mM IPTG (isopropyl-β-thiogalactoside) was added to the culture to induce the expression of hG-CSF gene. After 4 hour induction, 1 ml of the culture broth was aliquoted. The aliquoted broth was centrifuged at a speed of 6,000 rpm for 5 min at 4° C. to collect cells, which were then washed, centrifuged again at a speed of 6,000 rpm for 5 min at 4° C., and then resuspended in 0.2 ml of TE buffer. The mixture of 64 μl aliquot of cell suspension and 16 μl of sample buffer(Tris-HCl 60 mM: 25% glycerol (v/v): 2% SDS(v/v): 2-mercaptoethanol 14.4 mM: 0.1% bromophenol blue) was heated at 100° C. for 10 min, and then subjected to SDS-PAGE(sodium-dodecyl sulfate polyacrylamide gel electrophoresis) in separating gel. After SDS-PAGE, the gel was stained in a staining solution (Coomassie brilliant blue R 0.25 g/l: methanol 40% (v/v), acetic acid 7% (v/v)) for 2 hours, and destained two times in destaining solution (methanol 40% (v/v), acetic acid 7% (v/v)) for 2 hours each time. The SDS-PAGE did not show the protein band corresponding to hG-CSF protein.

EXAMPLE 3

Construction of the Recombinant Plasmid, pEDCSFmII

Based on the report by Devlin et al. that high G+C content in N-terminal portion of hG-CSF gene has inhibitory effect on transcription and translation of the gene (see: Devlin et al., Gene, 65:13–22 (1988)), primer 8: 5'-GCGAATTCATATGACTCCGTTAGGTCCAGCCAGC-3' (SEQ ID NO: 9) was prepared to obtain the gene which has lower G+C content such that the gene can be transcribed and translated efficiently in E. coli.

Figure 6:
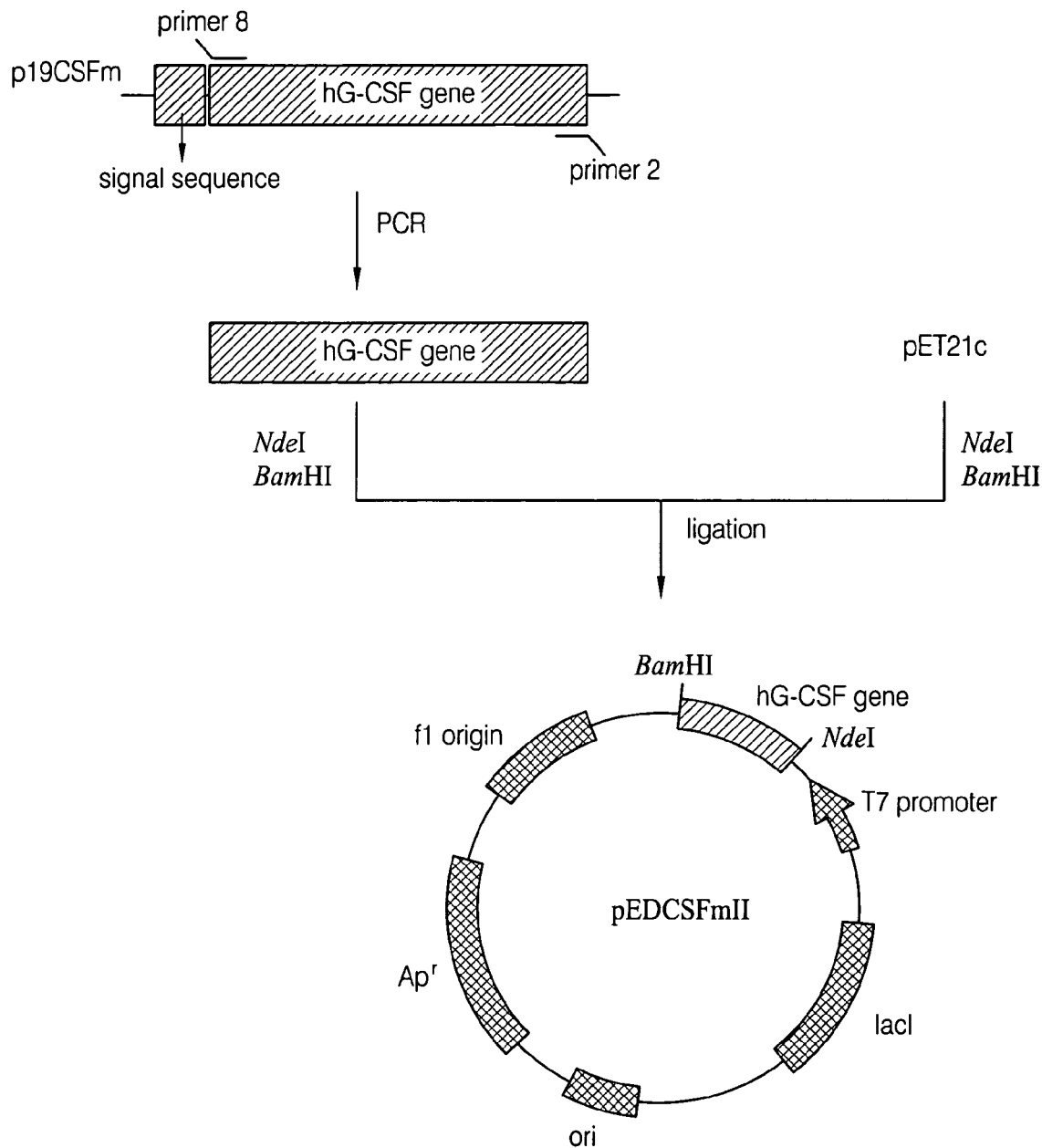
FIG. 6 shows a construction scheme and a genetic map for the plasmid pEDCSFmII.

Plasmid p19CSFm was amplified by PCR using primer 8 and primer 2. The resulting PCR product was digested with NdeI and BamHI, cloned into the same site of pET21c, and then transformed into *E. coli* XL1-Blue. The transformed *E. coli* XL1-Blue were selected on the LB agar medium containing ampicillin(50 µg/l) and the recombinant plasmid pEDCSFmII was obtained therefrom(see: FIG. 6). Comparing with the sequence of the fragment in pEDCSFm, the nucleotide sequence of the fragment in pEDCSFmII was found to be identical in N-terminal portion of the gene, meanwhile, be different in 6 nucleotide residues overall, which give rise the changes in 5 codons(ACC CCC CTG GGC CCT ACT CCG TTA GGT CCA: SEQ ID NO: 29).

Plasmid pEDCSFmII was transformed into *E. coli* BL21 (DE3) and its expression was analyzed. Culturing of transformed *E. coli*, and production and analysis of total protein were carried out as described in Example 2, and fractionation of insoluble aggregate was performed as follows. Cells obtained by centrifugation of 1 ml of culture broth were suspended in 0.5 ml of TE buffer (Tris-HCl 10 mM, EDTA 1 mM, pH 8.0), and then centrifuged again at a speed of 3,000×g for 5 min at 4° C. followed by resuspension in 0.2 ml of TE buffer. Cells were disrupted by using a ultrasonicator (Branson Ultrasonics Co., U.S.A.) and then centrifuged at a speed of 10,000×g for 10 min at 4° C. The supernatant was classified as soluble proteins and the pellet was dissolved in 0.2 ml of TE buffer and classified as insoluble proteins. The content of hG-CSF protein expressed in *E. coli* BL21(DE3) transformed with plasmid pEDCSFmII was identified to be as much as about 40% of total protein, and, most of hG-CSF protein produced was found to be insoluble aggregates with no biological activity.

EXAMPLE 4

Construction of the Recombinant Plasmid, pTrcSCSFmII

Figure 8:
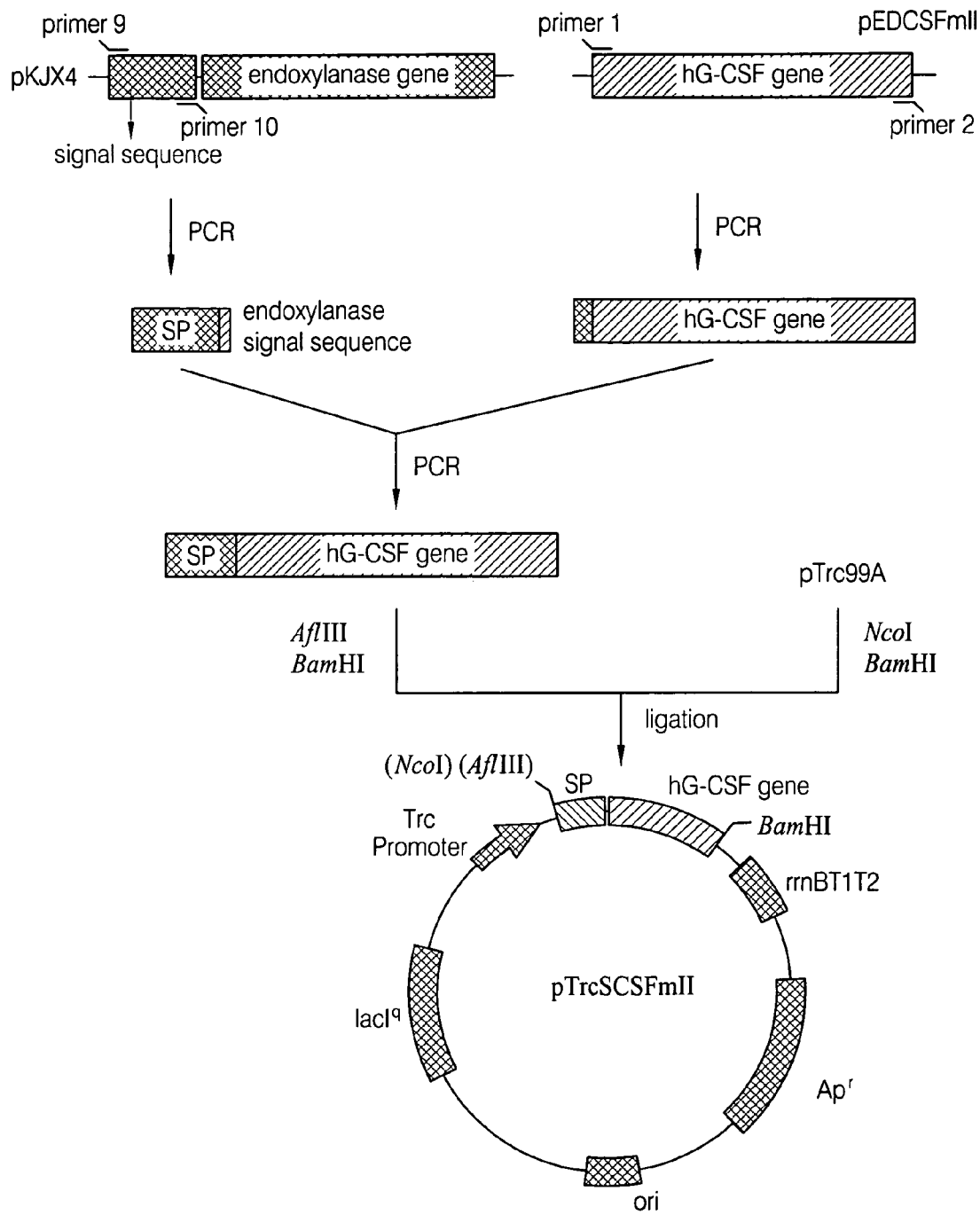
FIG. 8 shows a construction scheme and a genetic map for the plasmid pTrcSCSFmII.

The signal sequence of endoxylanase derived from *Bacillus* sp. was used for the secretion of hG-CSF protein from *E. coli*. To join the signal sequence of endoxylanase to the N-terminal of hG-CSF polypeptide by PCR, primer 9: 5'-GGAATTCACATGTTTAAG TTTAAAAAGAAATTC-3' (SEQ ID NO: 10), primer 10: 5'-GGCTGGACCTAACG-GAGTTGCAGAGGCGG-3' (SEQ ID NO: 11) and primer 11: 5'-GCAACCGCCTCTGCAACTCCGTTAGGTC-CAGCC-3' (SEQ ID NO: 12) were prepared, respectively. From PCR performed using primers 9 and 10, and endoxylanase gene-carrying plasmid pKJX4(see: Jeong et al., *Enzyme Microb Technol.* 22(7):599–605(1998)) as a target DNA, PCR product containing endoxylanase signal sequence was obtained, and from PCR performed using primers 2 and 11, PCR product containing hG-CSF gene was obtained. Again, PCR was performed using two PCR products obtained above, and primers 2 and 9 to obtain PCR product containing endoxylanase signal sequence-fused hG-CSF gene, which was then digested with two restriction enzymes, AflIII and BamHI. Also, the plasmid pTrc99A (Pharmacia Biotech Co., U.S.A.) carrying a strong inducible promoter, trc promoter, was digested with NcoI and BamHI, and then ligated with the above two PCR products. The ligation mixture was transformed into *E. coli* XL1-Blue. The transformants were selected on the LB agar medium containing ampicillin (50 µg/l) and the recombinant plasmid pTrcSCSFmII was obtained therefrom (see: FIG. 8). The nucleotide sequence of the N-terminal portion of hG-CSF gene was determined using an automatic DNA sequencer (ABI Prism model 377, Perkin Elmer Co., U.S.A.) (see: FIG. 9).

In order to analyze the secretion of hG-CSF protein in various strains of *E. coli*, the recombinant plasmid pTrcSCSFmII was transformed into *E. coli* BL21(DE3), *E. coli* HB101(F-hsdS20 (rk-, mk-) recA13 ara-14 proA2 lacY1 galK2 zpsL20 (strr) xyl1-5 mtl-1 supE44 λ-), *E. coli* MC4100(F-araD139 Δ (argF-lac) U169 rpsL150 (strr) relA1 flbB5301 deoC1 ptsF25 rbsR) and *E. coli* W3110(derived from *E. coli* K-12, λ-, F-, prototrophic). Each transformant was inoculated into 50 ml aliquots of LB medium containing ampicillin (50 µg/l), respectively, to perform the experiments for measuring expression level and protein analysis by the method described in Example 2. After induction with 1 mM IPTG, however, the cells began to lyse abruptly, and within 2 hours most cells were lysed. The cultures were centrifuged to obtain transformed *E. coli* cells and proteins were analyzed using SDS-PAGE to find out no protein corresponding hG-CSF protein was obtained.

EXAMPLE 5

Construction of the Recombinant Plasmid, pTrcKCSFmII

Figure 10:
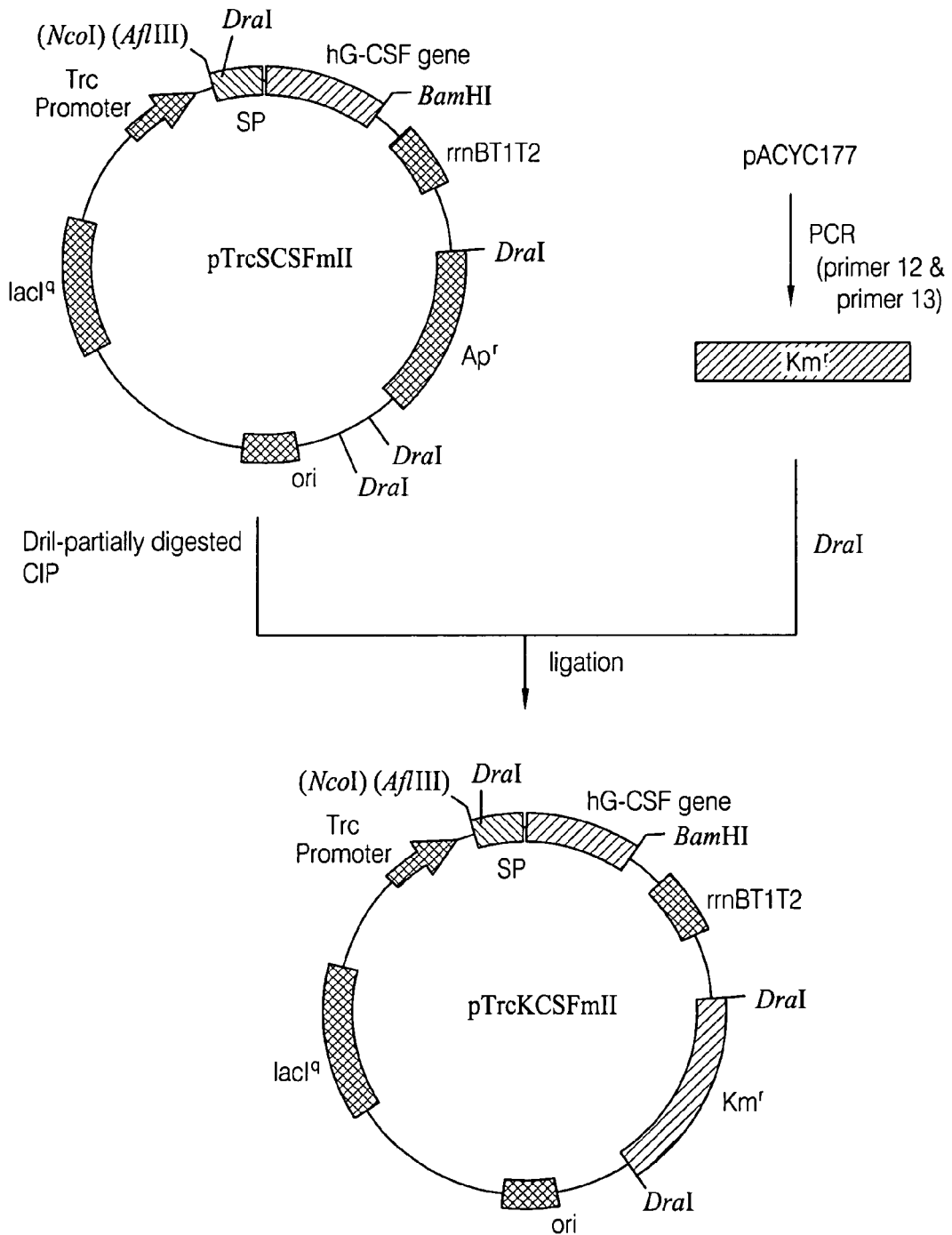
FIG. 10 shows a construction scheme and a genetic map for the plasmid pTrcKCSFmII.

Considering the fact that ampicillin resistance gene(Apr) in plasmid pTrcSCSFmII is coding for β-lactamase which is secreted to the periplasm of *E. coli*, it may be conjectured that there was a competition between β-lactamase and hG-CSF protein for secretion, and such competition brought about cell lysis observed in Example 4. Based on such hypothesis, kanamycin resistance gene(Kmr) was employed instead of ampicillin resistance gene(Apr) as a selection marker since kanamycin resistance gene encodes the non-secreted protein, still can be used as a selection pressure. In order to substitute ampicillin resistance gene(Apr) in plasmid pTrcSCSFmII with kanamycin resistance gene(Kmr), PCR was performed using primer 12: 5'-GCGAATTCTT-TAAAGCCACGTTGTGTCCTCAAA-3' (SEQ ID NO: 13) and peimer 13: 5'-GCGAATTCTTTAAATTAGAAAAACT-CATCGAGCATC-3' (SEQ ID NO: 14), and plasmid pACYC177 as a target DNA. The resulting PCR product containing kanamycin resistance gene was digested with DraI, and then ligated to the plasmid pTrcSCSFmII which was partially digested with DraI to remove ampicillin resistance gene. The ligation product was transformed into *E. coli* XL1-Blue. The transformants were selected on LB agar medium containing kanamycin (25 µg/l) and the recombinant plasmid pTrcKCSFmII was obtained therefrom (see: FIG. 10).

To analyze the secretion of hG-CSF protein, the recombinant plasmid pTrcKCSFmII was transformed into *E. coli* BL21(DE3), *E. coli* HB101, *E. coli* MC4100 and *E. coli* W3110. Each transformant was inoculated into 50 ml aliquots of LB medium containing kanamycin (25 µg/l), respectively, to perform the experiments for measuring expression level and protein analysis by the method described in Example 2, and same result was obtained as in Example 4 wherein pTrcSCSFmII was used. That is, with pTrcKCSFmII also, cells were lysed excessively upon induction with 1 mM IPTG and SDS-PAGE analysis of recovered protein showed no protein corresponding to hG-CSF protein. From the above studies, it has been found that the substitution of ampicillin resistance gene with kanamycin resistance gene exert no effect on avoiding cell lysis, therefore, another genetic manipulation which can solve the intrinsic problem of cell lysis caused by secretion of hG-CSF protein is necessary.

EXAMPLE 6

Construction of the Recombinant Plasmids, pTHSCSFmII and pTHKCSFmII

Figure 11:
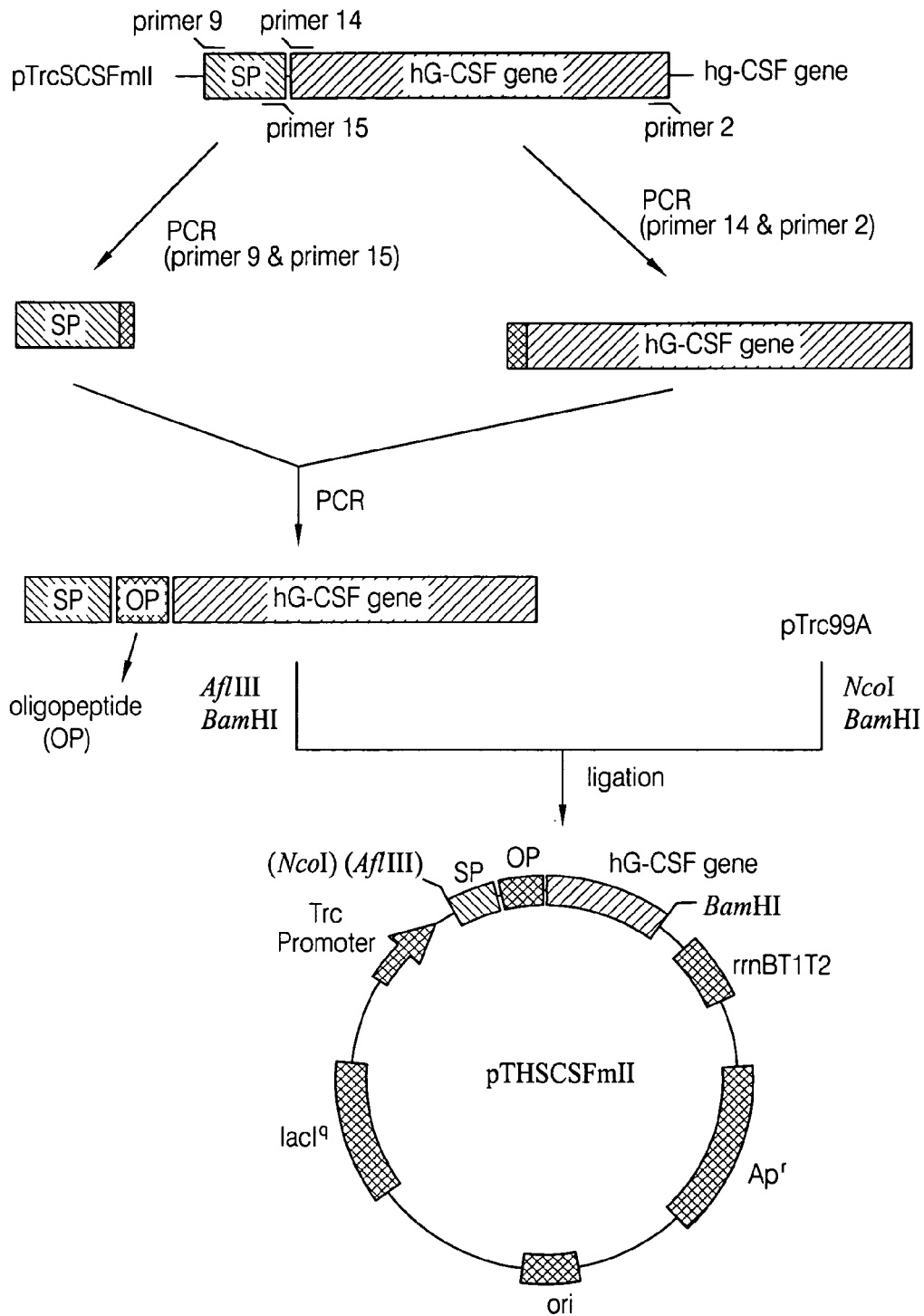
FIG. 11 shows a construction scheme and a genetic map for the plasmid pTHSCSFmII.

To facilitate E. coli to secrete hG-CSF protein without resulting in cell lysis, the strategy of inserting a small oligopeptide between endoxylanase signal sequence and hG-CSF protein was employed. For this purpose, PCR was performed using primer 14: 5'-CACCATCACCATATC-GAAGGCCGTACTCCGTTAGGTCCA-3' (SEQ ID NO: 15) and primer 15: 5'-GATATGGTGATGGTGATGGT-GCGGGCCAGCTGCAGAGGCGG-3' (SEQ ID NO: 16), and pEDSCSFmII as a target DNA. First, PCR with primers 14 and 2, and PCR with primers 15 and 9 were performed, respectively. Then, the two PCR products were mixed to be subjected to another PCR using primers 2 and 9, and the resulting product was digested with AflIII and BamHI to join into the NcoI/BamHI site of plasmid pTrc99A. After introducing the ligation product into E. coli XL1-Blue, the transformants were selected on a LB agar medium containing ampicillin (50 µg/l), and the recombinant plasmid pTH-SCSFmII was obtained therefrom (see: FIG. 11). FIG. 12 shows the nucleotide sequence and deduced amino acid sequence of the inserted DNA in the plasmid pTHSCSFmII, wherein the italic indicates the endoxylanase signal sequence and the bold indicates inserted oligopeptide sequence.

Figure 13:
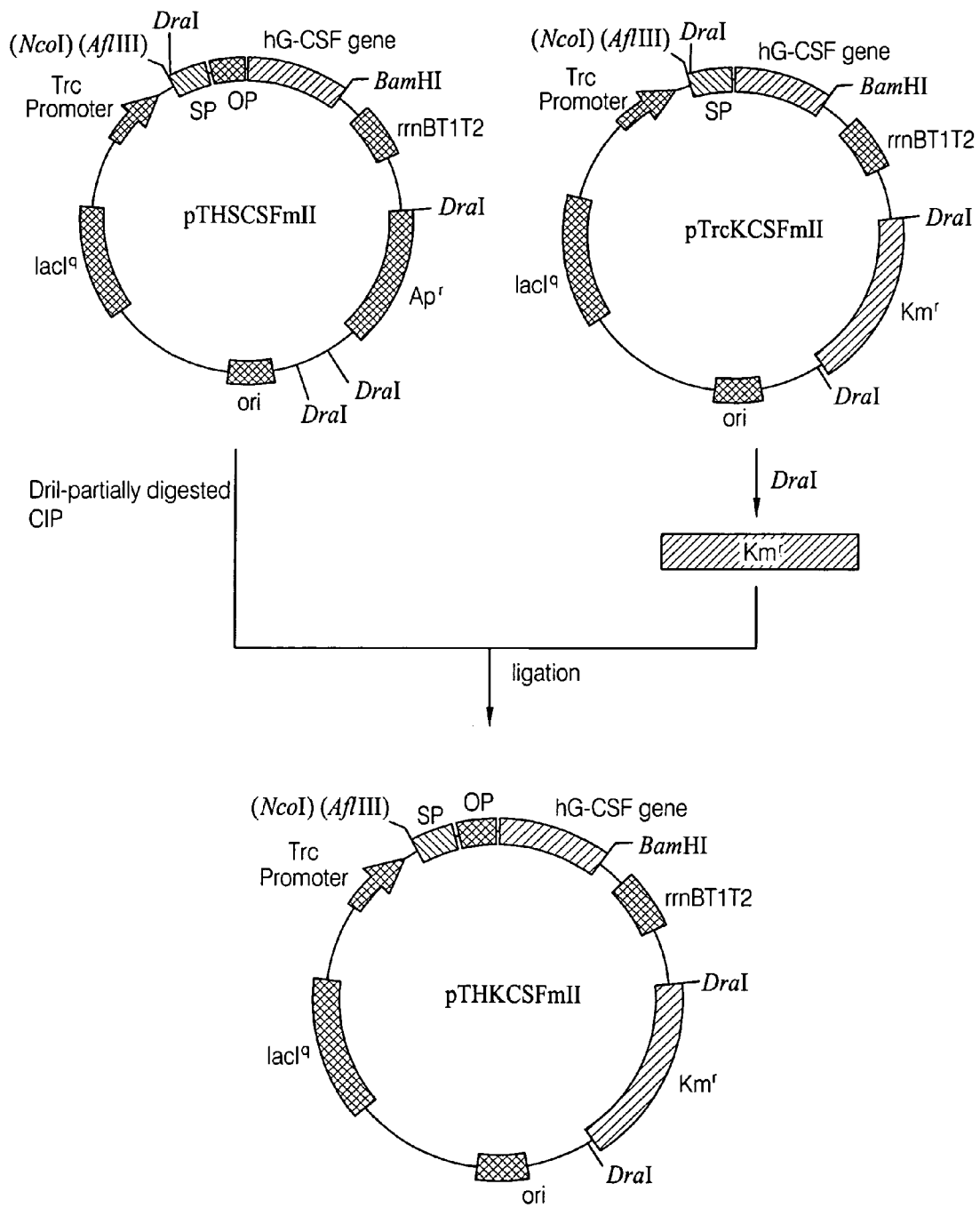
FIG. 13 shows a construction scheme and a genetic map for the plasmid pTHKCSFmII.

As similarly as in Example 5, in order to substitute ampicillin resistance gene(Apr) with kanamycin resistance gene(Kmr), the plasmid pTHSCSFmII was partial digested with DraI to remove ampicillin resistance gene(Apr) and then ligated with DNA fragment carrying kanamycin resistance gene obtained by digestion of pTrcKCSFmII with DraI. The ligation product was transformed into E. coli XL1-Blue. The transformants were selected on LB agar medium containing kanamycin (50 µg/l) and the recombinant plasmid pTHKCSFmII was obtained therefrom (see: FIG. 13).

EXAMPLE 7

Secretion of hG-CSF Fusion Protein from the Transformed E. coli Carrying the Recombinant Plasmid pTHKCSFmII To analyze the expression and secretion of hG-CSF fusion protein from pTHKCSFmII, the recombinant plasmid pTH-KCSFmII was transformed into E. coli BL21(DE3), E. coli HB101, E. coli MC4100 and E. coli W3110, respectively. Each transformant was cultured in 50 ml aliquots of LB medium under temperatures of 37° C. and 30° C., respectively, followed by analyses of secretion of the hG-CSF fusion protein as described in Example 2. After 4 hour induction of hG-CSF gene expression with 1 mM IPTG, 1 ml aliquots of culture broth were centrifuged to obtain the cells, which were then analyzed by SDS-PAGE for the expression of hG-CSF fusion protein to show the secretion of hG-CSF fusion protein from all the transformed E. coli. The contents and the secretion efficiencies of hG-CSF fusion protein secreted from the each transformed E. coli are shown in Table 1.

TABLE 1

Comparison of production and secretion of hG-CSF (%) in recombinant E. coli

| Host Cell | Content of hG-CSF (%) in Total Protein | | Secretion of hG-CSF (%) | |
|---|---|---|---|---|
| Culture Time | 30° C. | 37° C. | 30° C. | 37° C. |
| E. coli BL21 (DE3) | 22.7 | 22.1 | >98 | >98 |
| E. coli HB101 | 13.5 | 12.8 | 81 | 75 |
| E. coli MC4100 | 22.1 | 20.8 | >98 | >98 |
| E. coli W3110 | 10.5 | 10.0 | 77 | 66 |
| E. coli XL1-Blue | 9.4 | 8.8 | 56 | 51 |

To examine if the secreted hG-CSF protein has been processed correctly, i.e., if the signal sequence has been removed correctly, hG-CSF fusion prolein was isolated from the gel and its N-terminal amino acid sequence was detennined to be N'-Ala-Gly-Pro-His-His-His-His-His-His-Ile-Glu-Gly-Arg-Thr-C' (SEQ ID NO: 30), which is in agreement with the deduced amino acid sequence of N-terminal portion of hG-CSF fusion protein, indicating that the hG-CSF fusion protein was successfully secreted from E. coli. Of two temperature conditions, all the transformants showed higher secretion efficiency and highier hG-CSF protein content at 30° than 37° Of 5 strains of transformed E. coli, BL21(DE3) and MC4100 showed the highest production yield. Thus, E. coli MC4100 transformed with the recombinant plasmid pTHKCSFmII was named E. coli MC4100/pTHKCSFmE, which was deposited with the Korean Collection for Type Cultures(KCTC) affiliated to Korea Research Institute of Bioscience and Biotechnology (KRIBB), an international depository authority, under accession(deposition) No. KCTC 0754BP on Mar. 13, 2000.

The hG-CSF fusion polypeptide expressed in the transformed E. coli MC4100/pTHKCSFmII was processed during the secretion process to the periplasm through inner-membrane to remove endoxylanase secretion sequence, resulting in secretion of oligopeptide/hG-CSF fusion protein. The hG-CSF fusion protein can be isolated easily by using a nickel column due to 6 histidine residues in N-terminal portion of the fusion protein, and C-terminus of the oliopeptide in the fusion protein can be recognized by Factor Xa and the oligopeptide is cleaved off to give a complete hG-CSF protein.

As clearly illustrated and demonstrated above, the present invention provides an E. coli producing and secreting human granulocyte-colony stimulating factor(hG-CSF), a plasmid vector therefor, and a process for producing complete hG-CSF protein with high purity from the protein pool secreted by the said microorganism. In accordance with the invention, the hG-CSF protein can be prepared with high purity through rather simple process facilitating secretion of large amount of hG-CSF fusion protein into the periplasm, which does not require complicated processes such as solubilization and subsequent refolding required for isolation of the hG-CSF protein produced in cytoplasm as insoluble inclusion bodies by conventional techniques, thus, the hG-CSF protein can be widely used as an active ingredient in the development of supplementary agents for anticancer therapy.

It will be understood that the above description is merely illustrative of the preferred embodiment and it is not intended to limit the scope of the invention to the particular forms set forth, but on the contrary, it is intended to cover such alteratives, modifications and equivalents as may be included within the spirit and scope of the invention as defined by the claims.

What is claimed is:

1. A recombinant plasmid vector which comprises:
   a kanamycin resistance gene;
   a promoter;
   a nucleotide sequence coding for an endoxylanase signal sequence;
   a nucleotide sequence coding for an oligopeptide consisting of 13 amino acids, wherein 6 of the 13 amino acids are consecutive histidine residues; and,
   a human granulocyte colony stimulating factor (hG-CSF) gene.

2. The recombinant plasmid vector of claim 1, wherein the nucleotide sequence coding for the oligopeptide comprises a nucleic acid encoding SEQ ID NO: 28.

3. A recombinant plasmid vector pTHKCSFmII which comprises:
   a kanamycin resistance gene;
   a Trc promoter;
   a nucleotide sequence coding for a *Bacillus* sp. endoxylanase signal sequence;
   a nucleotide sequence coding for the oligopeptide of SEQ ID NO: 1; and
   a gene coding for a human granulocyte colony stimulating factor (hG-CSF) lacking its native signal sequence.

4. *E. coli* transformed with the plasmid vector pTHKCSFmII of claim 3.

5. The *E. coli* of claim 4, wherein the *E. coli* is selected from the group consisting of *E. coli* XL1-Blue, *E. coli* MC4100, *E. coli* BL21 (DE3), *E. coli* HB101 and *E. coli* W3110.

6. *E. coli* MC4100/pTHKCSFmII, deposited as KCTC 0754BP, wherein said *E. coli* is transformed with the plasmid vector pTHKCSFmII of claim 3.

7. A process for preparing a human granulocyte colony stimulating factor, which comprises the steps of:
   culturing *E. coli* transformed with the plasmid vector of claim 1 to obtain a human granulocyte colony stimulating factor fusion protein; and, treating the human granulocyte colony stimulating factor fusion protein with a protease to obtain a human granulocyte colony stimulating factor.

8. The process for preparing a human granulocyte colony stimulating factor of claim 7, wherein the plasmid vector is pTHKCSFmII.

9. The process for preparing a human granulocyte colony stimulating factor of claim 7, wherein the human granulocyte colony stimulating factor fusion protein is isolated from the protein pool obtained from the culture using a Ni-column.

10. The process for preparing a human granulocyte colony stimulating factor of claim 7, wherein the protease is Factor Xa.

11. The recombinant plasmid vector of claim 3, wherein said vector comprises the nucleotide sequence of SEQ ID NO: 26.

12. The recombinant plasmid vector of claim 3, wherein said gene comprises nucleotides 88 to 610 of the nucleotide sequence of SEQ ID NO: 18 and encodes the hG-CSF amino acid sequence of SEQ ID NO: 19.

13. The recombinant plasmid vector of claim 3, wherein said nucleotide sequence coding for said endoxylanase signal sequence comprises nucleotides 1–84 of the nucleotide sequence of SEQ ID NO: 26.

* * * * *

UNITED STATES PATENT AND TRADEMARK OFFICE
CERTIFICATE OF CORRECTION

PATENT NO. : 7,070,989 B2
APPLICATION NO. : 10/009792
DATED : July 4, 2006
INVENTOR(S) : Lee et al.

It is certified that error appears in the above-identified patent and that said Letters Patent is hereby corrected as shown below:

On the Title Page (56), at column 2, line 1, after "et al" please add --., --.

On the Title Page (56), at column 2, line 3, after "J" please add -- . --.

On the Title Page (56), at column 2, line 5, after "et al." please add -- , --.

At column 1, line 40, please replace "neurophil" with -- neutrophil --.

At column 1, line 51, please replace "dose" with -- does --.

At column 2, line 66, please replace "Bascillus-derived" with -- Bacillus-derived --.

At column 4, line 61, please replace "(SEQ" with -- SEQ --.

At column 4, line 62, please replace "NO:10," with -- NO: 1, --.

At column 5, line 31, after "gyrA96" please replace "thi" with -- the --.

At column 6, line 24, after "plasmid" please delete ",".

At column 7, line 39, after "endoxylanase" please delete ".".

At column 8, line 5, please replace "zpsL20" with -- rpsL20 --.

At column 8, line 5, please replace "xyl1-5" with -- xylI-5 --.

At column 8, line 39, please replace "peimer" with -- primer --.

At column 9, line 34, please replace "partial" with -- partially --.

At column 10, line 4 after "hG-CSF" please delete "(%)".

At column 10, line 17, please replace "prolein" with -- protein --.

At column 10, line 18-19, please replace "detennined" with -- determined --.

At column 10, line 24, please replace "highier" with -- higher --.

At column 10, line 25, please replace "30°" with -- 30°C. --.

UNITED STATES PATENT AND TRADEMARK OFFICE
CERTIFICATE OF CORRECTION

PATENT NO. : 7,070,989 B2
APPLICATION NO. : 10/009792
DATED : July 4, 2006
INVENTOR(S) : Lee et al.

It is certified that error appears in the above-identified patent and that said Letters Patent is hereby corrected as shown below:

At column 10, line 25, please replace "37°" with -- 37°C. --.

At column 10, line 29, please replace "pTHKCSFmE," with -- pTHKCSmll, --.

At column 10, line 42, please replace "oliopeptide" with -- oligopeptide --.

At column 10, line 65, please replace "alteranatives," with -- alternatives, --.

Signed and Sealed this

Ninth Day of January, 2007

JON W. DUDAS
*Director of the United States Patent and Trademark Office*

SEQUENCE LISTING

<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
<223> OTHER INFORMATION: Oligopeptide

<400> SEQUENCE: 1

Ala Gly Pro His His His His His His Ile Glu Gly Arg
 1               5                  10

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
gcgaattcat ggctggacct gccacccag                                    29

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
gcggatcctt attagggctg gcaaggtgg cg                                 32

<210> SEQ ID NO 4
<211> LENGTH: 50
<212> TYPE: DNA
<213> ORGANISM: Artificial Sequence
<220> FEATURE:
<223> OTHER INFORMATION: Primer

<400> SEQUENCE: 4
tcctcggggt ggcacagctt gtaggtggca cacagcttct cctggagcgc             50

<210> SEQ ID NO 5
<211> LENGTH: 50
<212> TYPE: DNA
<213> ORGANISM: Artificial Sequence
<220> FEATURE:
<223> OTHER INFORMATION: Primer

<400> SEQUENCE: 5
gctgtgccac cccgaggagc tggtgctgct cggacactct ctgggcatcc             50

<210> SEQ ID NO 6
<211> LENGTH: 50
<212> TYPE: DNA
<213> ORGANISM: Artificial Sequence
<220> FEATURE:
<223> OTHER INFORMATION: Primer

<400> SEQUENCE: 6
ctggctgggg cagctgctca ggggagccca ggggatgccc agagagtgtc             50

<210> SEQ ID NO 7

```
<211> LENGTH: 48
<212> TYPE: DNA
<213> ORGANISM: Artificial Sequence
<220> FEATURE:
<223> OTHER INFORMATION: Primer

<400> SEQUENCE: 7
agcagctgcc ccagccaggc cctgcagctg gcaggctgct tgagccaa        48

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
gaattcatat gacccccctg ggccctgcca gc                          32

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
gaattcatat gactccgtta ggtccagcca gc                          32

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
ggaattcaca tgtttaagtt taaaagaaa ttc                          33

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ggctggacct aacggagttg cagaggcgg                              29

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
gcaaccgcct ctgcaactcc gttaggtcca gcc                         33

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
```

```
gcgaattctt taaagccacg ttgtgtcctc aaa                                33
```

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14

```
gcgaattctt taaattagaa aaactcatcg agcatc                             36
```

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15

```
caccatcacc atatcgaagg ccgtactccg ttaggtcca                          39
```

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16

```
gatatggtga tggtgatggt gcgggccagc tgcagaggcg g                       41
```

<210> SEQ ID NO 17
<211> LENGTH: 507
<212> TYPE: DNA
<213> ORGANISM: Homo sapiens

<400> SEQUENCE: 17

```
atggctggac ctgccaccca gagccccatg aagctgatgg ccctgcagct gctgctgtgg    60
agtgcactct ggacagtgca ggaagccacc cccctgggcc ctgccagctc cctgccccag   120
agcttcctgc tcaagtgctt agagcaagtg aggaagatcc agggcgatgg cgcagcgctc   180
caggagaagc tggcaggctg cttgagccaa ctccatagcg ccttttcct ctaccagggg   240 ctcctgcagg ccctggaagg gatctccccc gagttgggtc ccaccttgga cacactgcag   300
ctggacgtcg ccgactttgc caccaccatc tggcagcaga tggaagaact gggaatggcc   360
cctgccctgc agcccaccca gggtgccatg ccggccttcg cctctgcttt ccagcgccgg   420
gcaggagggg tcctagttgc ctcccatctg cagagcttcc tggaggtgtc gtaccgcgtt   480
ctacgccacc ttgcccagcc ctaataa                                      507
```

<210> SEQ ID NO 18
<211> LENGTH: 615
<212> TYPE: DNA
<213> ORGANISM: Homo sapiens

<400> SEQUENCE: 18

```
atggctggac ctgccaccca gagccccatg aagctgatgg ccctgcagct gctgctgtgg    60
agtgcactct ggacagtgca ggaagccacc cccctgggcc ctgccagctc cctgccccag   120
agcttcctgc tcaagtgctt agagcaagtg aggaagatcc agggcgatgg cgcagcgctc   180
```

```
caggagaagc tgtgtgccac ctacaagctg tgccacccg aggagctggt gctgctcgga      240
cactctctgg gcatcccctg ggctcccctg agcagctgcc ccagccaggc cctgcagctg      300
gcaggctgct tgagccaact ccatagcggc cttttcctct accaggggct cctgcaggcc      360
ctggaaggga tctcccccga gttgggtccc accttggaca cactgcagct ggacgtcgcc      420
gactttgcca ccaccatctg gcagcagatg aagaactgg gaatggcccc tgccctgcag       480
cccacccagg gtgccatgcc ggccttcgcc tctgctttcc agcgccgggc aggagggggtc      540 ctagttgcct cccatctgca gagcttcctg gaggtgtcgt accgcgttct acgccacctt      600
gcccagccct aataa                                                        615
```

```
<210> SEQ ID NO 19
<211> LENGTH: 174
<212> TYPE: PRT
<213> ORGANISM: Homo sapiens

<400> SEQUENCE: 19

Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

```
<210> SEQ ID NO 20
<211> LENGTH: 531
<212> TYPE: DNA
<213> ORGANISM: Homo sapiens

<400> SEQUENCE: 20
atgacccccc tgggccctgc agctccctg ccccagagct tcctgctcaa gtgcttagag      60
caagtgagga gatccagggg cgatggcgca gcgctccagg agaagctgtg tgccacctac     120
aagctgtgcc accccgagga gctggtgctg ctcggacact ctctgggcat ccctgggct      180 cccctgagca gctgccccag ccaggccctg cagctggcag gctgcttgag ccaactccat      240
agcggccttt cctctacca ggggctcctg caggccctgg aagggatctc ccccgagttg       300
ggtcccacct tggacacact gcagctggac gtcgccgact ttgccaccac catctggcag      360
cagatggaag aactgggaat ggcccctgcc ctgcagccca cccagggtgc catgccggcc      420
```

```
ttcgcctctg ctttccagcg ccgggcagga ggggtcctag ttgcctccca tctgcagagc      480
ttcctggagg tgtcgtaccg cgttctacgc caccttgccc agccctaata a               531
```

<210> SEQ ID NO 21
<211> LENGTH: 175
<212> TYPE: PRT
<213> ORGANISM: Homo sapiens

<400> SEQUENCE: 21

```
Met Thr Pro Leu Gly Pro Ala Ser Ser Leu Pro Gln Ser Phe Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 22
<211> LENGTH: 45
<212> TYPE: DNA
<213> ORGANISM: Homo sapiens

<400> SEQUENCE: 22

```
atgactccgt taggtccagc cagctccctg ccccagagct tcctg                      45
```

<210> SEQ ID NO 23
<211> LENGTH: 15
<212> TYPE: PRT
<213> ORGANISM: Homo sapiens

<400> SEQUENCE: 23

```
Met Thr Pro Leu Gly Pro Ala Ser Ser Leu Pro Gln Ser Phe Leu
 1               5                  10                  15
```

<210> SEQ ID NO 24
<211> LENGTH: 135
<212> TYPE: DNA
<213> ORGANISM: Homo sapiens

<400> SEQUENCE: 24

```
atgtttaagt ttaaaaagaa attcttagtg ggattaacgg cagctttcat gagtatcagc      60
atgttttctg caaccgcctc tgcaactccg ttaggtccag ccagctccct gccccagagc      120
ttcctgctca agtgc                                                       135
```

```
<210> SEQ ID NO 25
<211> LENGTH: 45
<212> TYPE: PRT
<213> ORGANISM: Homo sapiens

<400> SEQUENCE: 25

Met Phe Lys Phe Lys Lys Lys Phe Leu Val Gly Leu Thr Ala Ala Phe
 1               5                  10                  15

Met Ser Ile Ser Met Phe Ser Ala Thr Ala Ser Ala Thr Pro Leu Gly
            20                  25                  30

Pro Ala Ser Ser Leu Pro Gln Ser Phe Leu Leu Lys Cys
        35                  40                  45

<210> SEQ ID NO 26
<211> LENGTH: 180
<212> TYPE: DNA
<213> ORGANISM: Homo sapiens

<400> SEQUENCE: 26
atgtttaagt ttaaaaagaa attcttagtg ggattaacgg cagctttcat gagtatcagc        60
atgttttctg caaccgcctc tgcagctggc ccgcaccatc accatcacca tatcgaggga       120
aggactccgt taggtccagc cagctccctg ccccagagct tcctgctcaa gtgcttagag       180

<210> SEQ ID NO 27
<211> LENGTH: 60
<212> TYPE: PRT
<213> ORGANISM: Homo sapiens

<400> SEQUENCE: 27

Met Phe Lys Phe Lys Lys Lys Phe Leu Val Gly Leu Thr Ala Ala Phe
 1               5                  10                  15

Met Ser Ile Ser Met Phe Ser Ala Thr Ala Ser Ala Ala Gly Pro His
            20                  25                  30

His His His His His Ile Glu Gly Arg Thr Pro Leu Gly Pro Ala Ser
        35                  40                  45

Ser Leu Pro Gln Ser Phe Leu Leu Lys Cys Leu Glu
    50                  55                  60
```